US008449922B1

(12) United States Patent
Rea et al.

(10) Patent No.: US 8,449,922 B1
(45) Date of Patent: May 28, 2013

(54) METHOD OF TREATING A CHEMICALLY SENSITIVE INDIVIDUAL

(76) Inventors: William James Rea, Dallas, TX (US); Bertie B. Griffiths, Rowlett, TX (US)

( * ) Notice: Subject to any disclaimer, the term of this patent is extended or adjusted under 35 U.S.C. 154(b) by 367 days.

(21) Appl. No.: 08/902,692

(22) Filed: Jul. 30, 1997

Related U.S. Application Data

(63) Continuation-in-part of application No. PCT/US96/01205, filed on Jan. 30, 1996, which is a continuation of application No. 08/380,063, filed on Jan. 30, 1995, now abandoned.

(51) Int. Cl.
*A61K 35/14* (2006.01)
*A61K 35/16* (2006.01)

(52) U.S. Cl.
USPC ............ 424/529; 424/530; 424/531; 424/520

(58) Field of Classification Search
USPC ............... 435/2; 424/520, 529, 534, 577, 578
See application file for complete search history.

(56) References Cited

U.S. PATENT DOCUMENTS 4,001,080 A * 1/1977 Goust et al. ................ 435/91.32
4,435,384 A * 3/1984 Warren
5,736,410 A * 4/1998 Zarling et al. ................ 436/172

OTHER PUBLICATIONS

Fahey et al., Clin. Exp. Immunol., 88:1-5, 1992.*
Osband et al., Immunol. Today, 11:103-105, 1990.*
Youdim et al., Clinical Ecology, vol. 7, 55-61, 1990.*
Barsky et al., Ann. Int. Med., 130:910-921, 1999, absrract thereof.*
Lane et al. "Chapter 66" from Handbook of Experimental Immunology in Four Volumes, vol. 2 : Cellular Immunology, ed. Weir et al., Blackwell Scientific Publications, 1984, p. 66.2.*
Griffiths, "Prospective Substitution of Transfer Factor with In Vitro Stimulated T lymphocytes", from The Twelfth Annual International Symposium on Man and His Environment in Health and Disease, Feb. 24-27, 1994, meeting presentation, www.aehf.com/articles/1994symp.html, pp. 6-7.*
Griffiths "A Laboratory Evaluation of the Phagocytic Function of Environmentally Sensitive Individuals". , from The Tenth Annual International Symposium on Man and His Environment in Health and Disease, Feb. 27-Mar. 1, 1992, meeting presentation, pp. 7-8 , www.aehf.com.*
Orme et al., "Multiple Chemical Sensitivity", American Council on Science and Health, pp. 1-24, 1994, from www.ACSH.org/publications/pubID.847pub_detail.ASP, retrieved Mar. 11, 2010.*
Hall, "Environmental Medicine, Not Your Average Specialty", Science Based Medicine, pp. 1-4, 2009, from www.sciencebasedmedicine.org/?p=2564, retrieved Mar. 11, 2010.*
Barrett, "Disciplinary Action against William Rea, M.D.", Casewatch, pp. 1-11, 2007, www.casewatch.org/board/med/rea/complaint.shtml, retrieved Mar. 11, 2010.*
Barrett, "Multiple Chemical Sensitivity: a Spurious Diagnosis", Quackwatch pp. 1-8, 2005, www.quackwatch.org/01QuackeryRelatedTopics/mcs.html, retrieved Mar. 11, 2010.*

Matthew Meyerson and Ed Harlow, Identification of $G_1$ Kinase Activity for cdk6, a Novel Cyclin D Partner, *Molecular and Cellular Biology*, Mar. 1994, pp. 2077-2086.
Matthew Meyerson, Greg H. Enders, Chin-Lee Wu, Li-Kuo Su, Carolyn Gorka, Camille Nelson, Ed Harlow and Li-Huei Tsai, A family of human cdc2-related protein kinases, *Oxford University Press*, May 4, 1992, pp. 2909-2917.
Michele Pagano, Rainer Pepperkok, Fulvia Verde, Wilhelm Ansorge and Giulio Draetta, Cyclin A is required at two points in the human cell cycle, *The EMBO Journal*, vol. 11 No. 3, Nov. 14, 1991, pp. 961-971.
Hans E. Parge, Andrew S. Arvai, Darren J. Murtari, Steven I. Reed, John A. Tainer, Human CksHs2 Atomic Structure: A Role for Its Hexameric Assembly in Cell Cycle Control, *Science*, vol. 262, Oct. 15, 1993, pp. 387-395.
Andrew W. Murray and Marc W. Kirschner, Dominoes and Clocks: The Union of Two Views of the Cell Cycle, *Science*, vol. 246, Nov. 1989, pp. 614-621.
Alexandaer Kamb, Nelleke A. Gruis, Jane Weaveer-Feldhaus, Qingyun Liu, Keith Harshman, Sean V. Tavtigian, Elisabeth Stockert, Rufus S. Day III, Bruce E. Johnson, Mark H. Skolnick, A Cell Cycle Regulator Potentially Involved in Genesis of Many Tumor Types, *Science*, vol. 264, Apr. 15, 1994, pp. 436-440.
Frederique Zindy, Eugenia Lamas, Xavier Chenivesse, Joel Sobczak, Jian Wang, Didier Fesquet, Berthold Henglein, and Christian Brechot, Cyclin A is Required in S Phase in Normal Epithelial Cells, *Biochemical and Biophysical Research Communications*, vol. 182, No. 3, 1992, Feb. 14, 1992, pp. 1144-1154.
Jeffrey A. Hadwiger, Curt Wittenberg, Helena E. Richardson, Miguel de Barros Lopes and Steven I. Reed, A family of cyclin homologs that control the $G_1$ phase in yeast, *Proc. Natl. Acad. Sci. USA*, vol. 86, Aug. 1989, pp. 6255-6259.
Steven I. Reed, G1-specific cyclins: in search of an S-phase-promoting factor, *TIG*, vol. 7, No. 3, Mar. 1991, pp. 95-99.
Michael Glotzer, Andrew W. Murray & Marc W. Kirschner, Cyclin is degraded by the ubiquitin pathway, *Nature*, vol. 349, Jan. 1991, pp. 132-138.
Kathleen L. Gould & Paul Nurse, Tyrosine phosphorylation of the fission yeast cdc2$^+$ protein kinase regulates entry into mitosis, *Nature*, vol. 342, Nov. 2, 1989, pp. 39-45.
Attila T. Lorincz & Steve I. Reed, Primary structure homology between the product of yeast cell division control gene CDC28 and vertebrate oncogenes, *Macmillian Journals Ltd.*, 1984.
Andrew W. Murray & Marc W. Kirschner, Cyclin synthesis drives the early embryonic cell cycle, *Nature*, vol. 339, May 25, 1989, pp. 275-280.

(Continued)

*Primary Examiner* — Ronald Schwadron

(74) *Attorney, Agent, or Firm* — Booth Albanesi Schroeder, LLC

(57) ABSTRACT

A method for treating a chemically sensitive individual is provided. The method includes the steps of: collecting a blood sample from the individual; isolating normal mixed T and B lymphocytes from the blood sample; propagating the isolated mixed T and B lymphocytes to obtain propagated lymphocytes; lysing the propagated lymphocytes to obtain a lysate; and administering the lysate to the individual. A therapeutic dose of the lysate can be determined by skin testing, and the dose can be administered subcutaneously. The effects of the treatment on the individual can be reflected by clinical tests such as hematological immunological profiles and symptom and signs scores.

18 Claims, 4 Drawing Sheets

OTHER PUBLICATIONS

Paul Nurse & Yvonne Bissett, Gene required in $G_1$ for commitment to cell cycle and in $G_2$ for control of mitosis in fission yeast, *Macmillan Journals Ltd.*, 1981.

Paul Nurse, Universal control mechanism regulating onset of M-phase, *Nature*, vol. 344, Apr. 5, 1990, pp. 503-508.

Curt Wittenberg, Katsunori Sugimoto, and Steven I. Reed, G1-Specific Cyclins of *S. cerevisiae*: Cell Cycle Periodicity, Regulation by Mating Pheromone, and Association with the $p34^{CDC28}$ Protein Kinase, *Cell*, vol. 62, Jul. 27, 1990, pp. 225-237.

Charles J. Sherr, Mammalian $G_1$ Cyclins, *Cell*, vol. 73, Jun. 18, 1993, pp. 1059-1065.

Mark J. Solomon, Michael Glotzer, Tina H. Lee, Michel Phillippe, and Marc W. Kirschner, Cyclin Activation of $p34^{cdc2}$, *Cell*, vol. 63, Nov. 30, 1990, pp. 1013-1024.

Helena E. Richardson, Curt Wittenberg, Fred Cross and Steven I. Reed, An Essential G1 Function for Cyclin-like Proteins in Yeast, *Cell*, vol. 59, Dec. 22, 1989, pp. 1127-1133.

Jonathan Pines and Tony Hunter, Isolation of a Human Cyclin cDNA: Evidence for Cyclin mRNA and Protein Regulation in the Cell Cycle and for Interaction with $p34^{cdc2}$.

Kim A. Nasmyth, FAR-Reaching Discoveries about the Regulation of START, *Cell*, vol. 63, Dec. 21, 1990, pp. 1117-1120.

Wang, et al., Hepatitis B virus integration in a cyclin A gene in a hepatocellular earcinoma, *Nature*, vol. 343, Feb. 8, 1990, pp. 555-558.

Dipty Desai, Yong Gu, and David O. Morgan, Activation of Human Cyclin-Dependent Kinases In Vitro, *Molecular Biology of the Cell*, vol. 3, May 1992, pp. 571-582.

Benjamin Lewin, Driving the Cell Cycle: M Phase Kinase, Its Partners, and Substrates, *Cell*, vol. 61, Jun. 1, 1990, pp. 743-752.

Tom Evans, Eric T. Rosenthal, Jim Youngblom, Dan Distel, and Tim Hunt, Cyclin: A Protein Specified by Maternal mRNA in Sea Urchin Eggs That is Destroyed at Each Cleavage Division, *Cell*, vol. 33, Jun. 1983, pp. 389-396.

Giulio Draetta and David Beach, Activation of cdc2 Protein Kinase during Mitosis in Human Cells: Cell Cycle-Dependent Phosphorylation and Subunit Rearrangement, *Cell*, pp. 17-26, 54:17-26, 1988.

Christian F. Lehner and Patrick H. O'Farrell, The Roles of *Drosophila* Cyclins A and B in Mitotic control, *Cell*, pp. 535-547, 61:535-547, 1990.

Jean Gautier, Mark J. Solomon, Robert N. Booher, J. Fernando Bazan, and Marc W. Kirschner, cdc25 is a Specific Tyrosine Phosphatase That Directly Activates $p34^{cdc2}$, *Cell*, vol. 67, Oct. 4, 1991, pp. 197-211.

Fang Fang and John W. Newport, Evidence that the G1-S and G2-M Transitions Are Controlled by Different cdc2 Proteins in Higher Eukaryotes, *Cell*, pp. 731-742, 66:731-742, 1991.

Frederick R. Cross, DAF1, a Mutant Gene Affecting Size Control, Pheromone Arrest, and Cell Cycle Kinetics of *Saccharomyces cerevisiae*, *Molecular and Cellular Biology*, Nov. 1988, pp. 4675-4684.

Definition of Chemical Sensitivity, William J. Rea, *Chemical Sensitivity*, vol. 4, pp. 7-16, 1994.

Practice Guidelines, *American Academy of Environmental Medicine*, 1992.

Practice Guidelines, *Pan American Allergy Society*, pp. 1-8, 1994.

\* cited by examiner

METHOD OF TREATING A CHEMICALLY SENSITIVE INDIVIDUAL

CROSS-REFERENCE TO RELATED APPLICATION

This application is a continuation in part of prior International Application No. PCT/US96/01205 filed Jan. 30, 1996 (designating and electing the United States), which was a continuation of U.S. application Ser. No. 08/380,063 filed Jan. 30, 1995, now abandoned.

TECHNICAL FIELD

This invention relates to a method of preparing and using an autogenous lymphocytic factor (ALF) for study, modification, and/or regulation of T and B lymphocyte parameters in a mammal, such as a human. The ALF is a substance derived from an individual's own normal T and B lymphocytes isolated from a blood sample and then propagated in a cell culture, which is then administered to the same individual. This invention modulates the abnormal function and levels of the individual's T and B lymphocytes and subsets as measured, for example, by direct flow cytometry, skin cell mediated immunity (CMI) tests, and/or symptoms and signs scores. These modulations were accomplished by an autogenous lymphocytic factor (ALF), in people who were: 1. sensitive to toxic chemicals (from environmental exposure); 2. allergic to pollen, dusts, molds and foods; and 3. those individuals with recurrent bacterial and viral infections.

SUMMARY OF INVENTION

This invention provides a clinical tool for the study, modification, and/or regulation of abnormal lymphocyte parameters, in a mammal, particularly a human, suffering from immune deregulation. T and B lymphocyte parameters include, for example, lymphocytic cell cycle and/or T and B lymphocyte and subset numbers. The status of the T and B lymphocyte parameters is reflected by other clinical tests, such as hematological and immunological profiles and symptom and sign scores.

The method involves determining the initial health status of an individual. The individual's initial health is best assessed by measuring the individual's T and B lymphocyte parameters, such as measuring the individual's lymphocytic cell cycle and/or measuring T and B lymphocytes and subset numbers. For example, by comparing an individual's abnormal lymphocytic cell cycle with the typical or normal cell cycle, the medical practitioner will be informed of the degree of cell cycle abnormality, and of what stage(s) or state(s) of the lymphocytic cell cycle are abnormal. The initial status of the individual's T and B lymphocyte parameters provides objective information that can be used to correlate with the individual's medical condition and be used as a possible explanation for the clinical manifestations of an individual suffering from a chronically suppressed or deregulated immune system. Furthermore, measuring information relating to an individual's lymphocytic T and B lymphocyte parameters, such as lymphocytic cell cycle and/or T and B lymphocyte and subset numbers, can be used to scientifically and objectively monitor the effects of clinical treatment with ALF on the individual's T and B lymphocyte parameters; or even to monitor changes that result from diet, other medications, or changes in the environment. In addition to T and B lymphocyte parameters, the initial health status of an individual is preferably also measured by hematological profiles, such as white blood cell count, immunological profiles, such as CMI scores, as and/or symptoms and signs scores.

According to the invention, autogenous lymphocytic factor (ALF) is a substance derived from an individual's own normal T and B lymphocytes isolated from a blood sample and then propagated in a cell culture. The ALF is then administered to the same individual. This ALF can modify the function and numbers of T and B cells and their subsets, hematological and immunological provides, as well as symptoms and signs scores of those individuals who are allergic to pollen, dust, molds, foods, chemicals (adverse reactions to ambient doses of toxic chemicals), and those with recurrent bacterial and non-HIV viral infections. According to one aspect of the invention, the ALF for the clinical treatment is in the form of a lysate prepared from normal mixed T and B lymphocytes grown in cell culture. For example, according to one embodiment of the invention, the lysate is prepared from the cell cultures of isolated T lymphocytes or B lymphocytes. According to yet another embodiment of the invention, the lysate is prepared from the cell cultures of one or more isolated subclasses of blood lymphocytes, for example, the $T_4$ or $T_s$ lymphocytes, or any combination of the lymphocytes subclasses. According to another aspect of the invention, the ALF comprises one or more enzymes isolated from a lysate prepared from lymphocytes grown in cell culture.

The ALF is clinically administered to the individual to study its effect on the individual's T and B lymphocyte parameters, such as cell cycle and cell numbers, and to modify or regulate the individual's abnormal lymphocytic cell cycle.

The regulatory effect of the ALF, if any, on the abnormal lymphocyte parameters is preferably objectively measured by subsequently determining the comparative change in the patient's lymphocyte parameters, such as lymphocytic cell cycle and/or T and B lymphocytes and subset numbers, hematological and immunological profiles, as well as symptoms and signs scores.

Of great importance is that the application of this invention is useful in the study of the immune system, and, furthermore, it is not limited to the treatment of a certain category of individuals. For example, the method can be applied to the study of and/or clinical treatment of individuals suffering from a suppressed, dysfunctional, or deregulated immune system for any number of possible causes. However, the emphasis of this invention is on the treatment of the individuals who have compromised immune systems that result in an abnormal susceptibility to environmental chemicals (chemically sensitive), pollens, dust, molds, food (allergies), bacteria and non-HIV viruses with recurrent infections.

It is anticipated that the invention can also be applied to the study of the prevention and/or treatment of some cancers. Being a biological response modifier, and having proven efficacies in certain non-HIV viral infections, the invention is also expected to stimulate the immune system of immunocompromised individuals, thus, it is expected that HIV-positive individuals might be benefited. The invention is expected to be useful in the study of the dysfunctional and suppressed immune system of HIV-positive individuals, which may also result in a therapy.

Although the description of this invention focuses on the human applications, the method of this invention can be easily extended to any mammal, so that it can also have veterinary uses.

These and other features, advantages, and objects of the present invention will be apparent to those working in the art upon reading the following detailed description of preferred embodiments and referring to the drawings.

BRIEF DESCRIPTION OF THE DRAWINGS

The attached drawings are incorporated into and form a part of the specification to illustrate several examples of the present invention. The drawings are only for the purpose of illustrating preferred and alternative examples of how the invention can be made and used and are not to be construed as limiting the invention to only the illustrated and described examples. The various advantages and features of the present invention will be apparent from a consideration of the drawings in which:

FIGS. 4a, 4b, and 4c represent a case history of a chemically sensitive patient treated with the present invention, wherein FIG. 4a shows the initial lymphocytic cell cycle of the patient, FIG. 4b shows the patient's lymphocytic cell cycle at three weeks following treatment with 0.1 cc doses of 1:10 diluted ALF administered about every four days by subcutaneous injections, and FIG. 4c shows the patient's lymphocytic cell cycle after six weeks of continued treatment with ALF.

DETAILED DESCRIPTION OF THE PREFERRED EMBODIMENT OF THE INVENTION

Figure 1:
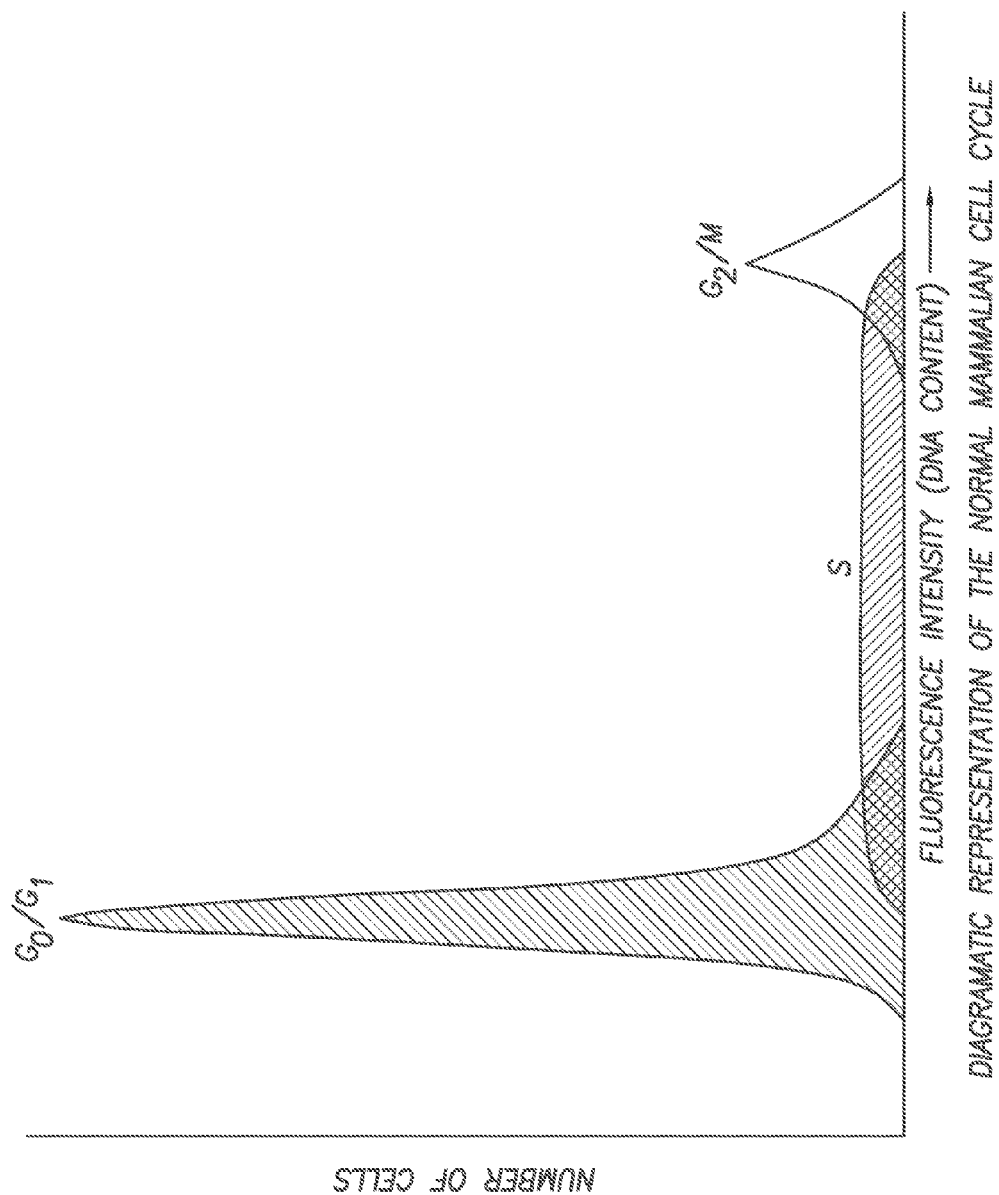
FIG. 1 is a diagrammatic representation of a normal mammalian cell cycle, wherein the overall cell doubling time is about 20-24 hours, the $G_1$ phase lasting about 8-12 hours, the S phase lasting about 6-8 hours, the $G_2$ phase lasting about 3-5 hours, and the M phase lasting about 0.5-1 hour.

In general, the process involves determining the individual's initial health status, including T and B lymphocyte parameters, comparing the measured parameters with normal parameters, preparing ALF from the patient's normal (non-cancerous or otherwise dysfunctional) lymphocytes, administering a dosage or series of dosages of ALF, and determining the effect of the ALF on the patient's T and B lymphocyte parameters.

According to a particular embodiment of the invention, one of the T and B lymphocyte parameters that is advantageously measured and followed in the lymphocytic cell cycle. This particular process includes measuring the patient's initial lymphocytic cell cycle, comparing the measured lymphocytic cell cycle with a normal or ideal lymphocytic cell cycle, preparing ALF from the patient's own normal lymphocytes, treating the individual with a therapeutic amount of the ALF, and determining the individual's lymphocytic cell cycle to observe any regulatory effect on the lymphocytic cell cycle and subsets.

Cell mediated immunity (CMI) skin tests are also used to help establish the patient's initial health status and to monitor the patient's progress with the ALF treatment. Cell mediated immunity (CMI) using seven (7) antigens and a negative control are used in standardized skin prick tests and read in 48 hours. The sign scores are measured where an average induration of 2 mm or more for an antigen is considered positive. The CMI scores are based on skin induration test reaction to the following seven (7) specific antigens: *Tetanus, Diphtheria, Streptococcus, Tuberculin, Candida, Trichophyton*, and *Proteus*; a negative control of pure water was employed.

The methodology and treatment can be repeated until the individual's lymphocytic cell cycle and/or T and B lymphocyte numbers are normalized. Furthermore, the methodology and treatment can be repeated to continuously attempt to counter the adverse effects on the lymphocytic cell cycle and/or T and B lymphocyte numbers of a chemically sensitive (C.S.) ill individual.

Determining and Following Lymphocytic Cell Cycle Changes

To determine the lymphocytic cell cycle, and the T and B lymphocytes and subset counts of the individual, heparinized lymphocytes can be used; and 100 µl of lysing buffer (Coulter) and gently mixed for approximately 15 sec; 2.0 ml of DNA stain with RNAse being added and mixed for 20 sec. The mixture is stained with propidium iodide at a concentration of 50 mg per ml allowing a staining period of 15 minutes and then analyzing by flow cytometry.

Cells tagged fluorometrically for DNA content are analyzed in a flow cytometer (e.g., a Coherent® cytometer or a Coulter® cytometer) with a laser beam turned to 448 nm. Fluorescence is measured electronically and recorded as a histogram. DNA distribution in the lymphocytic cell cycle is calculated on accumulated data by parametric analysis to produce a particular DNA histogram (for example, using Epics® software, provided with Coulter cytometer). The Coulter® cytometer with Epics® software system is available from Coulter Corporation, Miami, Fla., and such equipment and techniques are well known to those skilled in the art. This information provides a "snapshot" of the individual's present cell cycle. T and B cells and subsets counts are preferably also measured on the flow cytometer.

Figure 2A:
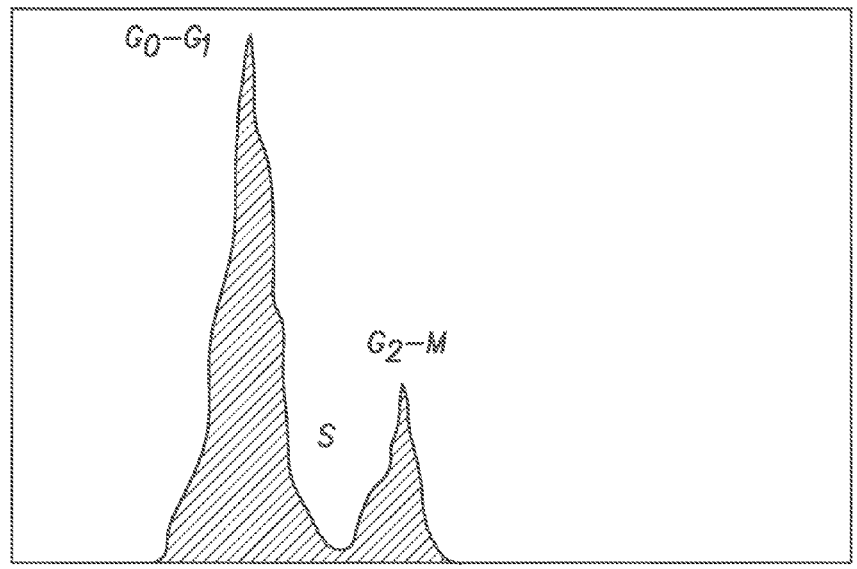
FIGS. 2a and 2b are representative cell cycle DNA histograms of human peripheral T lymphocytes obtained from "normal" or "control" volunteers.
Figure 2B:
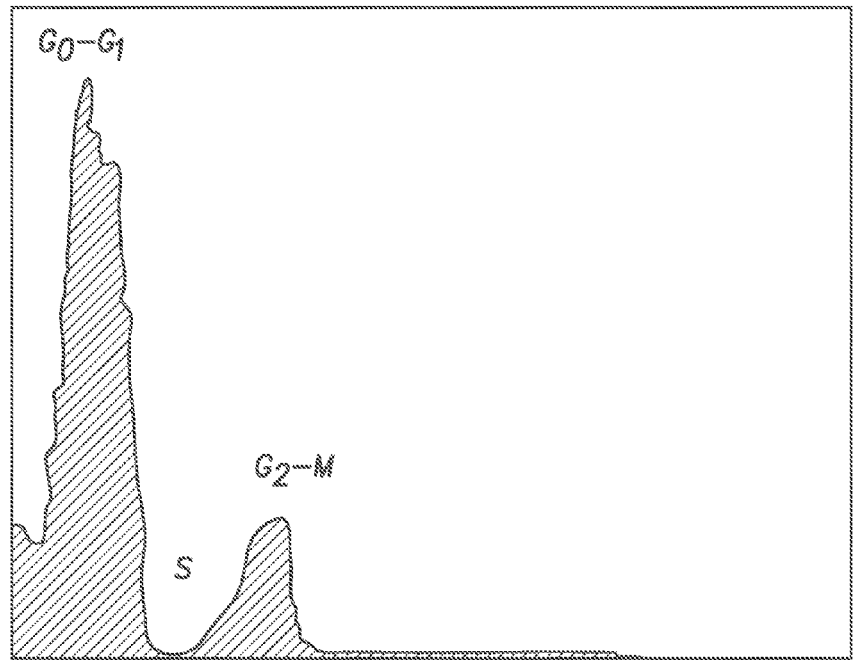
Figure 3A:
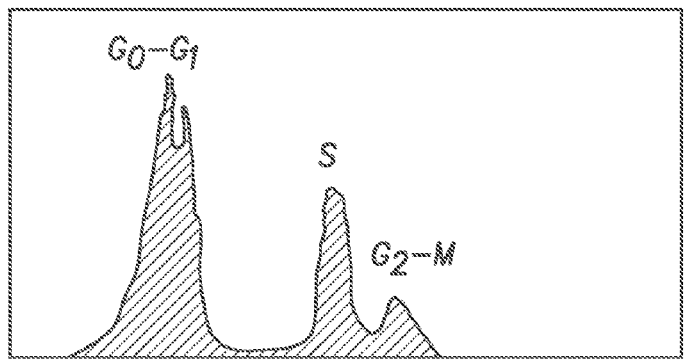
FIGS. 3a, 3b, and 3c show three different irregular cell cycle profiles chosen at random from environmentally compromised individuals.
Figure 3B:
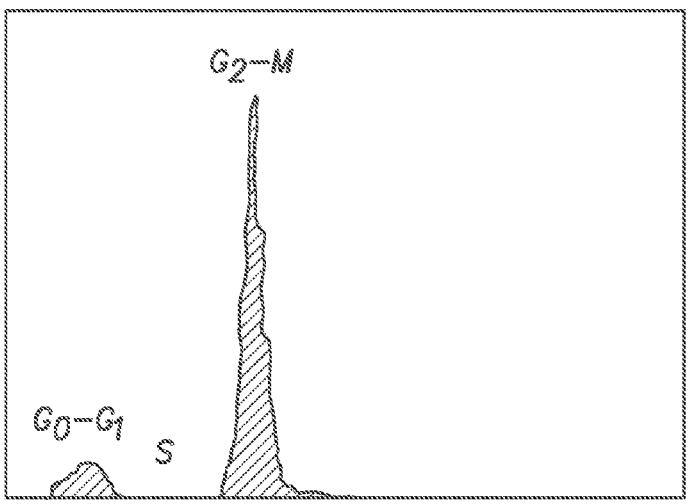
Figure 3C:
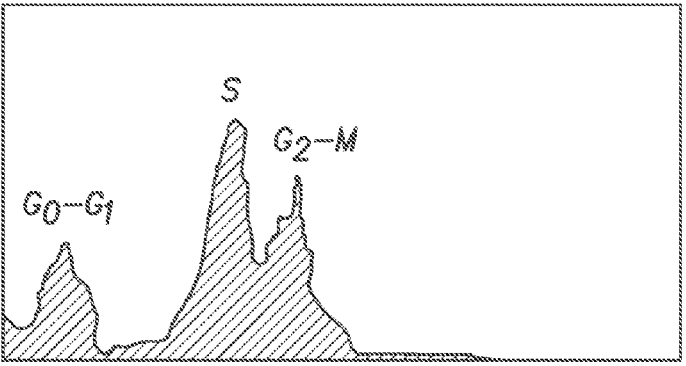

FIG. 2a is a normal DNA histogram of human peripheral T lymphocytes. FIG. 2b is a representative cell cycle DNA histogram obtained from "normal" or "control" volunteers. FIGS. 3a, 3b, and 3c show three different irregular cell cycle profiles chosen at random from environmentally ill patients.

Experience shows that the lymphocytic cell cycle measured according to this methodology will change an inconsequential amount during different times of the day indicating a circadian rhythm; however, substantially constant historical values were obtained for each control and patient at the same time of day. In particular, historical controls were established for ten patients by taking blood samples at the same time of day for ten days. However, in the absence of some kind of change, such as in environment, the advent of illness, or treatment according to the present invention, the lymphocytic cell cycle has also been observed to be substantially constant over many weeks and months. Thus, measurements according to the present studies were taken at the same time of day for each patient. Furthermore, it is possible to independently establish as a matter of trivial routine experiment the norms for the lymphocytic cell cycle.

The continuously-dividing lymphocyte blood cells used in the methodology of the invention are chosen for their stability, low replication levels, prompt response to stimuli, and ease of obtaining (for example, by venipuncture).

Preparation of ALF and Treatment with ALF

The presently preferred embodiment of the method for preparing the invention involves collecting blood from the ill individual and growing the normal lymphocytes in culture, harvesting the propagated cells, and collecting the biological regulator (ALF) from the cells for use in clinical treatments. The following steps are used:

1. Twenty (20) cc blood samples are collected from an ill human by venipuncture in heparinized tubes. The ill individual has abnormal T and B lymphocyte parameters, such as an abnormal lymphocyte cell cycle and/or abnormal T and B lymphocyte numbers and ratios.

2. Erythrocytes and neutrophils are separated from the blood lymphocyte samples by a modified Ficoll-Hypaque (sodium diatrizoate, polysucrose) density-gradient technique. (Gallard Schlesinger Chemical).

3. The erythrocytes and neutrophils are discarded, only the mixed T and B lymphocytes are utilized.

4. This preparation is centrifuged for 30 minutes at 500×g.

5. The lymphocyte layer (interphase between isolymph and plasma) is removed to sterile polystyrene tubes.

6. All lymphocytic layers are combined and washed three times with normal saline (0.9% sodium chloride) by centrifugation in a refrigerated centrifuge at 500×g for 20 minutes.

7. Cells are resuspended in normal saline and counted.

8. One (1) ml of these washed mixed lymphocytes (freshly drawn from the patient) is added to cell culture flasks containing 10 ml RPME 1640 cell culture medium.

9. The medium can optionally be supplemented with bovine calf serum (1 ml) to promote blastogenesis.

10. The culture is incubated at 37° C. and monitored daily until yield is approximately $5-8 \times 10^6$ cells per ml.

11. The culture suspension is transferred to a calibrated 50 ml conical tube and centrifuged for 30 minutes at 500×g.

12. The supernate is discarded, and the cell pellet is resuspended in 10 ml normal saline and washed three times by centrifugation for 30 minutes each time.

13. Each cell pellet is resuspended in approximately 2.0 ml normal saline and sonicated at 20 watts with a duty cycle of 50% for 60 sec.

14. The sonicated mixture is sterilized by millipore filtration.

15. The sterilized lysate (ALF) is stored at −20° C.

The concentrate ALF is to be diluted for therapeutic use as indicated by the DNA histograms and/or other hematological and immunological profiles of the individual and the recommendation of a physician. The lysate is a complex matrix including one or more enzymes from a cell sample of the patient who is treated. Because ALF is prepared from the patient's own genetic material, it is less likely to cause an adverse reaction when administered to the patient for clinical treatment.

Treatment with ALF

The particular therapeutic dose of the ALF for an individual depends on a number of medical and biological factors, including the type and degree of abnormality of the individual's cell cycle, T and B cell and subset counts and functions, the severity of the sensitivity of the patient, and the strength of the ALF employed. A therapeutic dose of ALF is defined as the amount of the sterilized lysate concentrate (ALF) required to stimulate blastogenesis of the patient's own cells in vitro, as compared to a known mitogen, for example, PHA. According to the presently most preferred embodiment, an individual's dose can also be clinically determined based on the amount the individual can tolerate without side effects. For example, in the presently most preferred embodiment of the invention, the ALF is typically diluted to 1:10 from the sterilized lysate concentrate with sterile normal saline solution or distilled water (some patients are sensitive to normal saline).

The individual patient is administered an intradermal skin test of 0.05 cc of the 1:10 diluted ALF to determine the patient's reaction and tolerance. If the skin test reveals sensitivity to ALF, the solution is further diluted either decimally or logarithmically and the skin test of step 2 repeated with the diluted preparation. This procedure is successively repeated until the skin test with the diluted ALF produces no adverse reaction. The most common therapeutic dose is 0.1 cc of the 1:10 dilution of ALF. However, as hereinafter described in detail, there is a range from about 1/1,000,000 dilution up to the concentrate of ALF for optimum treatment in the test patients.

The treatment dose of ALF is preferably administered by subcutaneous injection, however, any suitable means for administering the biological regulator (ALF) can be employed, including the intravenous route. Once a suitable dilution factor for the ALF has been determined, a half dose of 0.05 cc is administered to the patient. The patient is then closely observed for at least one-half hour to monitor for any adverse reaction to the dose. If no adverse reaction is observed, another half dose of 0.05 cc is administered to the patient to complete the dose of 0.1 cc.

The administration of the dose is typically repeated every four days ("q4d") until a total of twenty doses (total of 2.0 cc of the appropriately diluted ALF) has been administered to the patient.

At this time, evaluation of the lymphocytic cell cycle and/or T and B lymphocytes and subsets and their function is repeated and treatment dose is continued at the same level or adjusted higher depending on the measured changes in these T and B lymphocyte parameters.

Initial clinical testing indicates that a first treatment of therapeutic doses of ALF (0.1 cc of the properly diluted ALF) injected subcutaneously every four days can have a significant effect on improving the individual's T and B lymphocyte parameters. The regulatory effect can be objectively measured after the initial therapeutic treatment with ALF by determining the individual's lymphocytic cell cycle and the T and B lymphocytes and subset numbers, and also measured by cell mediated immunity by skin tests as well as symptoms and signs scores. These measurements provide further indication of whether further treatment with ALF would be beneficial and of the dosage of ALF that should be used.

According to a further aspect of the invention, one or more of the enzymes can be isolated using standard procedures well known to those skilled in the art, for example, affinity chromatographic techniques. These particular enzymes, once isolated, are expected to be chemically identical or substantially identical from one individual to the next of the same species; and perhaps even the same for different species of mammals. Thus, it is anticipated that the isolated enzymatic material can be used as a biological regulator without having to prepare the ALF from the cells of the same individual. While it would be naturally expected that one or more isolated particular enzymes may be more focused in their function, it may be that a synergistic action of a natural matrix of enzymes in a lysate may provide better therapeutic results.

Clinical Testing and Results

Twenty-five (25) individuals were used as normal controls. A total of 290 individuals were tested, including a first test group of 100 patients, and a second test group of 190 patients. The vast majority of these individuals were chemically sensitive, chronically ill patients, including those suffering from dermatitis, vasculitis, asthma, organic brain syndrome, gulf war syndrome, or immune system suppression, dysfunction, or deregulation. In addition, three (3) of the patients that were tested suffered from cancer, and one (1) was HIV positive.

About five percent (5%) of the individuals that otherwise would have been in the studies could not tolerate ALF. Except for noting this fact, these patients were not included in the data because they did not take enough ALF to be evaluated.

Some patients were initially presented with clinical manifestations including one or more of the following major symptoms:

Ocular: lacrimination, pruritus, swelling, puffiness;
Otic: fullness, noise, dizziness;
Nasal: congestion, sneezing, rhinorrhea, blowing;
Throat: lump, clearing, post nasal drip;
Immune: hypersensitivity reactions;
Musculo Skeletal: arthritis and arthralgia, fatigue, muscle pain;
Chest: pressure, cough;
Constitutional: weight loss, fatigue;
Headache: miliary, ethmoidal, frontal;
Neurological: insomnia, shortness of breath, depression.

The total of 290 chemically sensitive individuals that were investigated in these studies were affected principally by environmental incitants found in categories such as food, biological inhalants, and chemicals. They presented histories of varied backgrounds, but common among them was that all showed irregular cell cycles including T and B lymphocytes and subset numbers and functions. The DNA histogram cycles showed over or under accumulation of lymphocytes in one or more phases of the cell cycle of each individual. The T and B lymphocytes of the affected individual are "stuck" in a particular phase, resting, synthesizing, or multiplying too much in the $G_0$-$G_1$, S, $G_2M$ phase, respectively. The individual often manifested symptoms peculiar to the phase(s) affected.

Significant changes were typically observed in patients treated with ALF. Changes were observed in improvement of overall clinical manifestations and immune studies. With regard to clinical manifestations, minimal symptoms (which were improved over the onset symptoms) continued after three weeks of continued therapy with ALF. Immunologically, there were significant regulations of lymphocytic cell cycles, especially from one phase of the cycle to another, and changes in T and B lymphocyte cell numbers and functions. Patients became less sensitive to exposures and more tolerant to specific incitants. As treatment continued, in general, in about six weeks a more drastic shift toward that of a normal profile was observed.

Figure 4A:
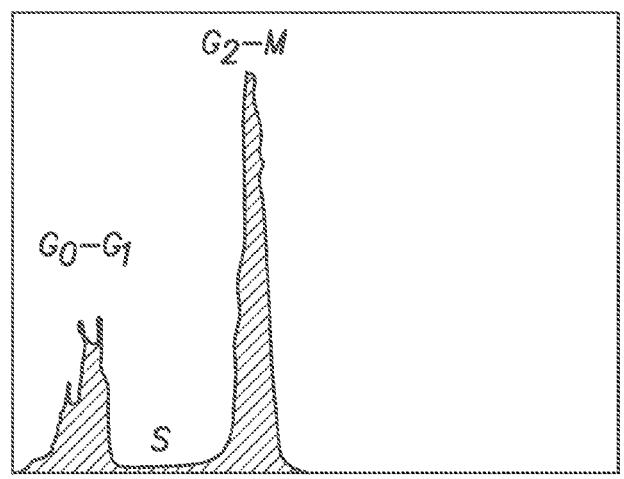
Figure 4B:
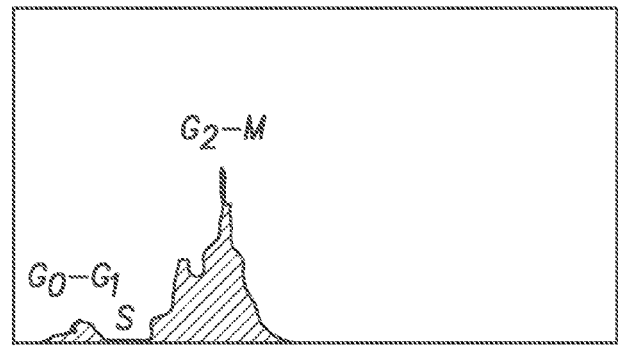
Figure 4C:
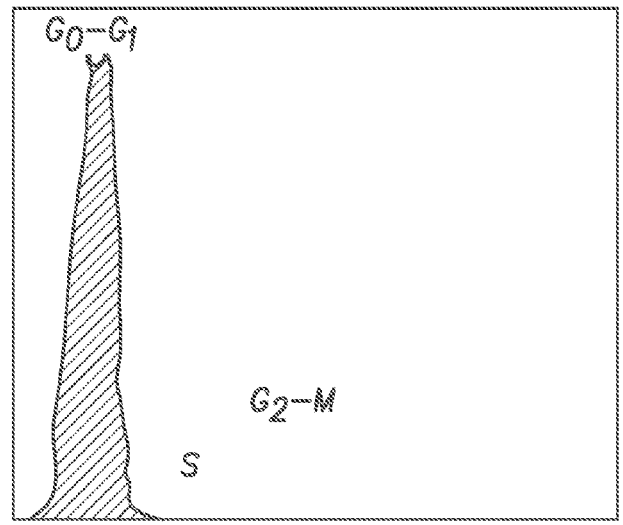

FIGS. 4a, 4b, and 4c represent a case history of a chemically sensitive patient treated according to the patent invention. FIG. 4a shows the initial lymphocytic cell cycle of the patient. FIG. 4b shows the patient's lymphocytic cell cycle at three weeks following treatment with 0.1 cc doses of 1:10 diluted ALF administered about every four days by subcutaneous injections. FIG. 4c shows the patient's lymphocytic cell cycle after six weeks of continued treatment with ALF.

The cell cycle presents a reflection of the status of the T lymphocytes in an individual. According to the presently most preferred embodiment of the invention, the method can be used to establish a basis for the regulation of an individual's T lymphocytes that are observed to be irregular due to varied incitants; thus restoring normal T lymphocyte functions and the ability of a compromised individual to cope with multiple insults to his/her immune system. Of great importance is that the application is not limited to the treatment of a certain category of individuals, but applies to "normal" individuals as well as individuals that are compromised by varied incitants. For example, preliminary data with the cancer patients and the one HIV-positive patient shows that further clinical testing of ALF for treatment of these types of diseases is warranted. Thus, the methodology has application in further research studies on the immune system, separate and apart from the treatment of any specific disease or symptom.

First Test Group of 100 Chemically Sensitive Patients Treated with ALF

TABLES 1-10 show the laboratory results in the first 100 patients studied with ALF. There was an 88% improvement ($p<0.001$) in symptoms and signs scores. This improvement highly correlated with improvement of total T lymphocytes and the $T_4$ and $T_8$ lymphocytes ($<0.05$) and cell mediated immunity T-cell function ($p<0.001$).

One-hundred six (106) chemically sensitive patients including 80 females, 26 males, from 3 to 77 years old with an average age of 48, who had been on a stable treatment regimen including massive avoidance in pollutants in air, food and water; rotary diets of organic food and nutritional supplementation developed for their specific nutritional needs were studied. The majority of the patients were also on injection therapy for sensitivity to biological inhalants, foods, and chemicals, although some could not tolerate this type of therapy. All patients were improved with their present treatment but not where they wanted to be in their health and were looking for a booster for improvements of health.

In general, treatment with autogenous lymphocytic factor (ALF) is accomplished by separating the patient's own T and B lymphocytes and growing them in cell cultures. This process takes approximately six weeks. After there are sufficient and robust lymphocytes, they are fractured mechanically, and the immunity factors are removed, sterilized, and standardized. Then the patient takes injections every four days for a period of time. The patients were monitored for their presenting signs and symptoms, including the severity and frequency of their hypersensitivity reactions, recurrent infections, fatigue, difficulty concentrating, arthritis, headaches, gastrointestinal upset and episodes of depression. Intolerance and side effects were also monitored. Laboratory parameters followed before, during, and after the therapy were T and B lymphocytes, cell mediated immunity (CMI), complete blood count (CBC), and standard blood chemistry tests (SMAC-22).

One hundred (100) of the patients could tolerate ALF, including 75 females and 25 males. The sex and age distribution of this first group of patients is shown in TABLE 1.

Since there were no measurement units for autogenous lymphocytic factor, these were arbitrarily determined as the amount of the concentrated ALF that would stimulate blastogenesis in vitro as compared to a known mitogen, for example, PHA. As shown in TABLE 2, the normal dosage of ALF in this series was 0.1 cc of the 1:10 diluted ALF, which was administered every four days ("cc/q4d"). However, 37% needed a build up dosage in the range of anywhere from 0.15 cc to 1 cc of the 1:10 diluted ALF to exhibit a clinical response in symptoms and signs, while 16% needed a dilution dosage of 0.10 cc in the range of 1:100 to 1:1,000,000 dilution of the concentrated ALF. TABLE 2. This later group was extremely sensitive and would react violently with flu-like symptoms and increase in their hypersensitivities if the dose was too high.

As one can see in TABLE 3, the length of time before clinical response was anywhere from one injection (or the first dose) to sixteen months of treatment based on the administration of a dose every four days. The average time of clinical response in symptoms and signs was 7.4±3.8 months. The average therapy dosage was 6.44 cc±3.79 cc of the 1:10 diluted ALF with a range from 2-25 cc until a significant clinical response in symptoms and signs was observed ("volume" dosage data normalized based on the standard 1:10 dilution of the ALF). TABLE 4.

Symptoms and signs scores are shown in TABLE 5 and TABLE 6. The severity of hypersensitive reaction, fatigue, recurrent infections, depression, concentration seemed to improve significantly. TABLE 5. The frequencies of hypersensitive reaction, recurrent infections, fatigue, headaches, and depression were also altered. TABLE 6. Significant improvement occurred in 88% of the patients with a p<0.001.

T and B lymphocytes and their subsets were evaluated before and after treatment with ALF. TABLES 7 and 8 reflect that there was significant (p<0.05) change in the total lymphocyte count and in the $T_4$ and $T_8$ lymphocyte counts in the ninety-two patients measured. As shown in TABLE 8, the autogenous lymphocytic factor (ALF) appears to act as a modulator since total lymphocytes and the $T_4$, and $T_s$ lymphocytes significantly elevated or decreased in order to obtain normalization.

Cell mediated immunity (CMI) was evaluated using a scoring system of the combination of the size of the wheals and the increase in the number of the wheals. Data was compiled from seventy eight of the patients in the first test group. The data shown in TABLE 9 of CMI scores 10; is based on skin tests for reaction to seven antigens: *Tetanus, Diphtheria, Streptococcus, Tuberculin, Candida, Trichophyton,* and *Proteus*; a negative control of pure water was also employed. Each skin test was measured after 48 hours. The CMI data shows a clinically and statistically significant change in the cell mediated immunity observed after treatment with ALF according to the methodology of this invention. As shown in TABLE 9, the mean diameter of the cell mediated immune response to the antigens nearly doubled after six weeks of treatment with ALF according to the methods described; more particularly, the CMI score was 5.46±5.81 before treatment with ALF, while after ALF treatment, the CMI score was 9.28±7.25. This response achieved a high statistical significance of p<0.001. After treatment with ALF, 74% of the chemically sensitive patients increased their CMI scores while 12% showed no change and 14% decreased their scores. However, there remains the puzzling fact that 18% of the patients who had no change or a lowering of the CMI still had improved clinical signs and symptoms. Without being limited by any theoretical explanation, it is speculated that the ALF treatment modulates other non-immune factors that lead to clinical improvement.

Side effects of ALF occurred in 6 (5%) (5 females, 1 male, 46-57 years old, average 52 years old) patients who could not tolerate ALF and had to stop the treatment. As shown in TABLE 10, the patients had pain and irritation in the throat, burning in eyes, nausea, chest tightness, heart palpitations, flu-like symptoms, headache, fatigue, and chills. One also had a heightened odor and food sensitivity. These six patients were not included in the first test group data because they did not take enough ALF to be evaluated.

Chemically sensitive individuals have long searched for laboratory parameters that might reflect part of their problems and subsequently substances that would improve their health. It has been previously reported that a subset of chemically sensitive patients had low $T_8$ suppressor cells and others had suppressed cell mediated immunity. Decreasing the total body pollutant load in air, food, and water intake aided in improving these parameters as well as their clinical signs and symptoms. However, though some chemically sensitive patients were totally well after this regime, some still needed injection therapy for their secondary sensitivities to biological inhalant, food, and chemical sensitivity as well as nutrition supplementation in order to maintain health. A third type of patient had tried all of these modalities and still had not achieved the level of health they desired. This was the group that was reported in this study. This group of chemically sensitive patients were much more sensitive than the previous groups who cleared on avoidance and injection therapy. These patients would react to the minutest exposure of most ambient chemicals, biological, inhalants (molds, pollen, etc.). All were sensitive to the majority of foods, and the food injections (if they could tolerate), though helpful did not eliminate the problem. As shown in TABLES 5 and 6, the hypersensitivity reactions markedly decreased or disappeared. What was even more surprising was the fact that recurrent infection, fatigue, headaches, depression, concentration, even gastrointestinal upsets were also improved.

One fact that was fascinating was the fact that eight patients did get immediate improvement on the first injection. One of these patients, a physician's wife, was universally food and chemically sensitive. She had been trying to get decent end points for injection therapy for several months. After the first injection of ALF, her skin returned to normal whealing; the fatigue and depression lifted. After administration of ALF, she was able to get injections with good results for her food and biological inhalant sensitivities. She immediately became well and able to work again for the first time in years. This continued effect has lasted for two years as long as she continued her treatment with ALF. There appears to be a switch that was turned on in these eight patients allowing immediate improvement of health.

T-suppressor, T-helper cells and total lymphocytes cells improved. The low ones increased, and the high ones decreased thus suggesting that ALF is a modulator rather than a stimulator. Without being limited by the theoretical explanation, it is speculated that ALF alters the activities of the helper and suppressor T-cells.

In summary, the preliminary data from the first test group of 100 patients studied suggested that ALF is a significant improver of a subset of chemically sensitive patients.

Second Test Group of 190 Chemically Sensitive Patients Treated with ALF

TABLES 11-21 show the clinical analysis of a second test group of 190 chemically sensitive patients who have been treated with the autogenous lymphocytic factor (ALF). (As before, about 5% of the patients who could not tolerate ALF were excluded from the test group data because they did not take enough ALF to be evaluated.)

A total of one hundred ninety (190) patients could tolerate ALF, including 131 females and 59 males. The sex and age distribution of this second test group of chemically sensitive patients is shown in TABLE 11.

Since there were no measurement units for autogenous lymphocytic factor, these were arbitrarily determined as the amount the concentrated ALF that would stimulate blastogenesis of the patient's own cells in vitro, as compared to a known mitogen, for example, PHA. The normal dosage of ALF in this series was 0.1 cc of the 1:10 dilution of ALF, which was administered every four days ("cc/q4d"). However, 44% needed a build up dosage in the range of anywhere from 0.15 cc to 1 cc of the 1:10 dilution of ALF to exhibit a response, while 9% needed a dilution dosage of 0.10 cc in the range of a 1:20 to 1:1,000,000 dilution of ALF. TABLE 12. This later group was extremely sensitive and would react violently with flu-like symptoms and increase in their hypersensitivities if the dose was too high.

As shown in TABLE 13, the length of time before significant clinical response was anywhere from one injection (or the first dose) to 38 months of treatment based on the administration of a dose every four days. The average time for clinical response in symptoms and signs was 14.6 months. The average total dosage was 11.27 cc of ALF with a range from 1-38 cc until a significant clinical response occurred ("volume" dosage data normalized based on the standard 1:10 dilution of the ALF). TABLE 14.

Symptoms and signs scores are seen in TABLE 15 and TABLE 16. Significant improvement occurred in 85% of the patients with a $p<0.001$. The severity of hypersensitive reaction, fatigue, recurrent infections, depression, concentration seemed to improve significantly. The frequencies of hypersensitive reaction, recurrent infections, fatigue, headaches, and depression were also altered.

T and B lymphocytes and their subsets were evaluated before and after treatment with ALF. TABLES 17 and 18 reflect that there was significant ($p<0.01$) change in the total lymphocyte count and in the $T_4$ and $T_8$ lymphocyte counts in the 96 patients measured. The data presented in TABLES 17 and 18 is limited to those numbers of patients who exhibited abnormal T and B lymphocyte parameters for the specific category. The autogenous lymphocytic factor (ALF) appears to act as a modulator since total lymphocytes, and $T_4$ and $T_8$ lymphocytes in particular, significantly elevated or decreased in order to obtain normalization.

Cell mediated immunity (CMI) was evaluated using a scoring system of the combination of the size of the wheal and the increase in the number of the wheals. Data compiled from ninety-three (93) patients in the second test group of this study showed clinically and statistically significant changes in the cell mediated immunity ("CMI") observed after treatment with ALF according to the methodology of this invention. The data in TABLE 19 of CMI scores is based on skin tests for reaction to seven antigens: *Tetanus, Diphtheria, Streptococcus, Tuberculin, Candida, Trichophyton,* and *Proteus*; a negative control of pure water was also employed. Each skin test was measured after 48 hours. As shown in TABLE 19, the total number of the antigen responses of the CMI tests tended to increase after treatment with ALF according to the methods described herein. This response achieved a high statistical significance of $p<0.001$ compared with the decrease in total sign number.

TABLE 20 shows a general clinical diagnosis of the 190 patients in the second test group in this study. TABLE 21 shows a more specific classification of the clinical symptoms of the 190 patients in the second test group in this study, including: neurological systems (N.S.); Cardio/Vascular (C.V.); Gastro/Intestinal (G.I.); Genital/Urinary (G.U.); Muscular/Skeletal (M.S.); and other diagnoses.

Data compiled from the blood sample analyses taken from the patients in the study show clinically and statistically significant changes in T and B cell profiles of the patients after treatment with ALF according to the methods described herein. The measured changes in T and B cell profiles is objective evidence of the beneficial consequence of the regulation of the cell cycle according to the inventive methodology.

Again, there is a high correlation of improvement of clinical signs and symptoms with the T and B cells and CMI's after treatment with ALF. There were significant improvements in specific signs and symptoms like hypersensitivity reaction, recurrent infections, and depression.

Treatment of One HIV Positive Patient with ALF

TABLE 22 shows a case study of one 50 year old white female HIV-positive patient; she had improved markedly over the five-month period of treatment with 0.025 cc of 1:10 diluted ALF every four days. In particular; her CMI score changed from −1 to +3, her white blood count (WBC) improved, her T and B lymphocyte profile improved, and her various clinical symptoms (Sx) improved. As noted, she took ALF for 5 months, then stopped. All clinical symptoms exacerbated for 3 weeks. After restarting the ALF treatment, all her clinical symptoms disappeared again.

Treatment of Cancer Patients with ALF

TABLE 23 shows the presently available data regarding CMI scores, white blood count (WBC), T and B lymphocyte numbers and ratios that were observed in the testing of the patients known to suffer from cancer.

Theoretical Discussion

Without limiting the invention to any particular theoretical explanation, the regulation of the cell cycle in eucaryotes seems to take place at two main transition points, prior to DNA replication at a point in the $G_1$ phase, termed the restriction point, and prior to cytokinesis at the $G_2$-M phase boundary. The progression of the cell cycle from one phase to the other appears to be mediated by specialized protein kineses called cyclin-dependant kinases (CDK's).

To date, at least seven kinds of CDK's have been defined in the medical literature: CDC 2-8, that are able to participate in the control of $G_1$-S phases, and also in a number of positive and negative feedback loops. The CDK's are observed to play very significant roles in the $G_1$-S and $G_2$-M transitions during the mammalian cell cycle. Here, they regulate by phosphorylation, a number of key substrates that subsequently activate a transition from $G_1$ and from $G_2$ to M phases. The catalytic subunits alone of these CDK's are not active, and require the influence of positive regulatory subunits to ensure biochemically active protein kinase holoenzymes. The positive regulatory subunits employed to this end are called cyclins. The activity of CDK's is, therefore, regulated by both cyclins and specific phosphorylation and dephosphorylation.

Cyclins were identified originally by their cyclic accumulation and destruction at defined points during the cell cycle. Cyclins are classified as A, B, C, D, E, F, $G_f$, and H based on their amino acid sequences, and in some instances, on genetic complementation experiments in yeasts. The influence of the cyclins are expressed differently. Cyclin A exhibits its influence through the S-M phase of most cells, while Cyclin B (which is conserved from yeasts to human cells) propels cells into mitosis. Both the A and B cyclins are degraded at the M phase by ubiquitin (Ub)-dependent proteolysis. $G_1$ cyclins (CINI, CIN2 CIN3) are assumed to associate with a P34cdc2 homologue, P34cdc28, driving yeast cells into S phase.

It is reasonable then to assume that the incitant(s) that lead to immuno-incompetence of these individuals are capable of inactivating the particular enzyme(s) cyclin-dependent kinases which are instrumental in catalyzing the T lymphocytes from phase to phase of the cell cycle.

The treatment of lasting importance would be reasonably thought of a biological response modifier that would stimulate CDK's and regulate the cell cycle and the enzymes of purine and pyrimidine nucleotide synthesis, since it is now generally accepted that these enzymes are elevated during the S phase. Without limiting the invention, we believe that ALF mediates this function. The mechanism(s) of action has not yet been elucidated. However, it has been documented that the human cells contain a regulatory protein, CKS protein, which is a genetic suppressor of temperature sensitive CDK mutations. There are two isoforms of this CKS protein, namely CKSH,1 and CKSH,2. Without limiting the invention, it is believed that CKSH,2 protein binds to the catalytic subunit of the CDK's, and is essential for their biological function.

The invention might be applied to some cancer patients based on the concept that the progression of cells from one phase of the cell cycle to another is closely regulated by many biochemical controls. These controls act on the transcription cyclin genes, degradation of cyclin proteins, and by kinase subunits that have been modified by phosphorylation. In the absence of such positive controls, the genome of the cells may become compromised; cells with unstable genomes may develop into cancer cells. It is anticipated that treatment with ALF will regulate cell proliferation, stabilizing the genome, thereby eliminating the possibility of the evolution of cancer cells.

Being a biological response modifier, ALF is expected to stimulate the immune system of immuno-compromised individuals, thus, it is expected that HIV positive individuals will be benefited therapeutically, as it did from the case study of the patient presented herein.

Scope of Invention

The description and drawings of the specific examples above do not point out what an infringement of this patent would be, but are to provide at least one explanation of how to make and use the invention. Numerous modifications and variations of the preferred embodiments can be made without departing from the scope and spirit of the invention. Thus, the limits of the invention and the bounds of the patent protection are measured by and defined in the following claims.

TABLE 1

The Distribution of Sex and Age of 100 Patients with A.L.F.

| AGE | F | M | TOTAL |
|---|---|---|---|
| 1- | 2 | 3 | 5 |
| 11- | 1 |  | 1 |
| 21- | 3 | 5 | 8 |
| 31- | 10 | 2 | 12 |
| 41- | 16 | 7 | 23 |
| 51 | 21 | 7 | 23 |
| 61- | 20 | 1 | 21 |
| 71- | 2 |  | 1 |
| TOTAL | 75 | 25 | 100 |

TABLE 2

ALF Dosage

| | Patient | | Dosage (cc/q4d) (minimum dose in cc that triggers blastogenesis) | |
|---|---|---|---|---|
| | No. | % | Range | Mean |
| Normal | 47 | 47 | 0.1 | 0.1 |
| Build up | 37 | 37 | 0.15-1.0 | 0.3 |
| Dilution | 16 | 16 | 0.01-0.00001 | 0.05 |

TABLE 3

The Distribution of Time of Therapy

| | | | | Months | | | | | | | |
|---|---|---|---|---|---|---|---|---|---|---|---|
| | 2 | 3 | 4 | 5 | 6 | 7 | 8 | 9 | 10 | 11 | >12 |
| No. Patients | 8 | 14 | 11 | 7 | 7 | 6 | 10 | 6 | 4 | 7 | 20 |

Average therapy time: 7.4 ± 3.8 months
Range: 2-16 months

TABLE 4

The Distribution of Dosage of Therapy

| | | | | Dosage (cc) | | | | | | | |
|---|---|---|---|---|---|---|---|---|---|---|---|
| | 2 | 3 | 4 | 5 | 6 | 7 | 8 | 9 | 10 | 11 | >12 |
| No. Patients | 8 | 13 | 15 | 6 | 8 | 11 | 10 | 6 | 4 | 7 | 14 |

Average therapy 6.44 ± 3.79 cc
Range: 2-25 cc

TABLE 5

Scale of Clinical Symptoms and Signs of
The Patient After ALF Treatment
(Severity)

| | Improvement | | No Charge | | Worsening | | Total |
|---|---|---|---|---|---|---|---|
| Symptoms | No. | % | No. | % | No. | % | Patients |
| Hypersensitive Reaction | 63 | 63 | 33 | 33 | 1 | 1 | 100 |
| Recurrent Infection | 38 | 57 | 29 | 43 | 0 | 0 | 67 |
| Fatigue | 60 | 68 | 27 | 31 | 1 | 1 | 88 |
| Lock of Concentration | 43 | 54 | 36 | 46 | 0 | 0 | 79 |
| Arthritis | 19 | 44 | 23 | 54 | 1 | 2 | 43 |
| G.I. Upset | 29 | 40 | 43 | 60 | 0 | 0 | 72 |
| Headache | 28 | 44 | 33 | 53 | 2 | 3 | 64 |
| Depression | 42 | 58 | 30 | 42 | 0 | 0 | 72 |

TABLE 6

Scale of Clinical Symptoms and Signs of
The Patient After ALF Treatment
(Frequency)

| | Improvement | | No Charge | | Worsening | | |
|---|---|---|---|---|---|---|---|
| Symptoms | No. | % | No. | % | No. | % | Total Patients |
| Hypersensitive Reaction | 38 | 38 | 62 | 62 | 0 | 0 | 100 |
| Recurrent Infection | 26 | 39 | 41 | 61 | 0 | 0 | 67 |
| Fatigue | 38 | 43 | 50 | 57 | 0 | 0 | 88 |
| Lack of Concentration | 20 | 25 | 59 | 75 | 0 | 0 | 79 |
| Arthritis | 11 | 26 | 32 | 74 | 0 | 0 | 43 |
| G.I. Upset | 21 | 29 | 51 | 69 | 0 | 0 | 72 |
| Headache | 19 | 30 | 45 | 70 | 0 | 0 | 64 |
| Depression | 30 | 42 | 42 | 58 | 0 | 0 | 72 |

TABLE 7

The Changes of T & B Profile of 92 Patients Treated with ALF

|  | TOTAL LYMPHOCYTES | $T_{11}$ | $T_4$ | $T_8$ | $T_4/T_8$ | $B_4$ |
|---|---|---|---|---|---|---|
| BEFORE | 2112 ± 632 | 1624 ± 457 | 930 ± 45 | 439 ± 58 | 2.3 ± 0.8 | 188 ± 102 |
| AFTER | 2232 ± 678 * | 1634 ± 544 | 1027 ± 297  | 478 ± 189  | 1.3 ± .4 | 171 ± 120 | n = 92
* $p < 0.05$
** $p < 0.01$

TABLE 8

T Lymphocyte Subsets 92 Patients After ALF Treatment

|  | TOTAL LYMPHOCYTES | | $T_B$ | | $T_4$ | | $T_1$ | |
|---|---|---|---|---|---|---|---|---|
|  | No. | % | No. | % | No. | % | No. | % |
| INCREASE | 52 | 57 | 41 | 46 | 53 | 58 | 55 | 60 |
| DECREASE | 40 | 43 | 51 | 54 | 39 | 42 | 37 | 40 |
| P |  | <0.05 |  | <0.05 |  | <0.05 |  | <0.01 |

TABLE 9

CMI Results with ALF Effect

CMI Scores (Number and Size, $\bar{x} \pm SD$)

| NO. PATIENTS | BEFORE ALF | AFTER ALF | P |
|---|---|---|---|
| 78 | 5.46 ± 5.81 | 9.28 ± 7.25 | <0.001 |

CMI Positive Score
(Number and Size) After ALF

| | NO. PATIENTS | % | P |
|---|---|---|---|
| INCREASE | 58 | 74 | <0.001 |
| NO CHANGE | 9 | 12 | |
| DECREASE | 11 | 14 | |

The Relationship Between CMI and
Clinical Symptom and Sign Improvement

| | IMPROVE-MENT | | NO IMPROVE-MENT | | |
|---|---|---|---|---|---|
| | NO. | % | NO. | % | P |
| CMI INCREASE | 56 | 72 | 2 | 3 | <0.001 |
| CMI NO CHANGE & DECREASE | 14 | 18 | 6 | 8 | |

TABLE 10

Side Effects of ALF - (5% of Patients Can Not Tolerate ALF)

1. PAIN AND IRRITATION IN THROAT, BURNING IN THE EYES
2. NAUSEA
3. CHEST TIGHTNESS AND HEART PALPITATION
4. FLU-LIKE SYMPTOMS, HEADACHE, FATIGUE, CHILL
5. INCREASE IN FOOD AND ODOR SENSITIVITY

TABLE 11

190 Patients with ALF

| | No. | % |
|---|---|---|
| Female | 131 | 69 |
| Male | 59 | 31 |
| Age: | 2-76 years old | |
| Mean: | 46.8 years old | |

TABLE 12

ALF Dosage

| Patient | | Dosage (cc/q4d) (minimum dose in cc that triggers blastogenesis) | |
|---|---|---|---|
| | No | % | Range |
| Normal | 88 | 46 | 0.1 (1:10) |
| Build up | 84 | 44 | 0.15-1.0 (1:10) |
| Dilution | 18 | 9 | 0.1 (1:20, 1:10$^2$-1:10$^6$) |

TABLE 13

The distribution of period of ALF therapy

| Month | No. Patients | % |
|---|---|---|
| 1-3 | 27 | 14.2 |
| 4-6 | 19 | 10.0 |
| 7-9 | 25 | 13.2 |
| 10-12 | 20 | 10.5 |
| 13-15 | 11 | 5.8 |
| 16-18 | 21 | 11.1 |
| 19-21 | 21 | 11.1 |
| 22-24 | 7 | 3.7 |
| 24-26 | 14 | 7.4 |
| 27-29 | 11 | 5.8 |
| 30-32 | 5 | 2.6 |
| 33-36 | 9 | 4.7 |

Average: 14.6 months (Range 1-37 months)

TABLE 14

The Distribution of dosage of ALF

| Dosage (cc) | No. Patient | % |
|---|---|---|
| 1-5 | 45 | 23.7 |
| 6-10 | 59 | 31.1 |
| 11-20 | 66 | 34.7 |
| 21-30 | 19 | 10 |
| 31-40 | 1 | 0.5 |
| Total | 190 | 100 |

Average: 11.27 (cc)
Range: 1-38 (cc)

TABLE 15

Scale of Clinical Symptoms and Signs of The C.S. Patient After ALF Treatment (Severity)

| Symptoms | Improvement No. | % | No Changes No. | % | Worsening No. | % | Total Patients |
|---|---|---|---|---|---|---|---|
| Hypersensitive Reaction | 51 | 56.7 | 33 | 36.7 | 6 | 6.7 | 90 |
| Recurrent Infection | 33 | 50.8 | 27 | 41.5 | 5 | 7.7 | 65 |
| Fatigue | 58 | 71.6 | 17 | 20.99 | 6 | 7.1 | 81 |
| Lack of Concentration | 42 | 57.5 | 29 | 39.7 | 2 | 2.7 | 73 |
| Arthritis | 20 | 44.4 | 22 | 48.9 | 3 | 6.7 | 45 |
| G.I.Upset | 31 | 44.4 | 33 | 45.8 | 7 | 9.7 | 72 |
| Headache | 30 | 40.5 | 38 | 51.4 | 6 | 8,1 | 74 |
| Depression | 44 | 63.8 | 22 | 31.9 | 3 | 4.3 | 69 |

TABLE 16

Scale of Clinical Symptoms and Signs of The Patient After ALF Treatment (frequency)

| Symptoms | Improvement No. | % | No Changes No. | % | Worsening No. | % | Total Patients |
|---|---|---|---|---|---|---|---|
| Hypersensitive Reaction | 28 | 36.4 | 46 | 59.7 | 3 | 3.9 | 77 |
| Recurrent Infection | 27 | 46.6 | 27 | 46.6 | 4 | 6.9 | 58 |
| Fatigue | 36 | 47.4 | 37 | 48.7 | 3 | 3.9 | 76 |
| Lack of Concentration | 23 | 33.8 | 43 | 63.2 | 2 | 2.9 | 68 |
| Arthritis | 13 | 32.5 | 24 | 60.0 | 3 | 7.5 | 40 |
| G.I. Upset | 23 | 37.1 | 35 | 56.5 | 4 | 6.5 | 62 |
| Headache | 24 | 38.1 | 34 | 54.0 | 5 | 7.9 | 63 |
| Depression | 34 | 54.8 | 26 | 41.9 | 2 | 3.2 | 62 |

TABLE 17

T & B Lymphocytes Parameters Changes After ALF

|  | (N) | Before (mean ± SE) | After |
|---|---|---|---|
| WBC | 25 | 4180 ± 404.1** | 4828 ± 1164.6 |
| Lymphs | 34 | 1350 ± 225.1** | 1573.2 ± 448.2 |
| T11 | 32 | 989.4 ± 198.1** | 1182.6 ± 331.2 |
| T4 | 30 | 518.2 ± 107.2** | 689.5 ± 200.1 |
| Ratio of T4/T8 | 46 | 3.62 ± 0.99** | 2.71 ± 1.04 |
| T8 | 52 | 248.6 ± 63.3** | 354.3 ± 124.9 |
| B4 | 35 | 54.8 ± 17.0** | 121.3 ± 78.7 |

**--$P < 0.01$ (Change compared with before ALF therapy)

TABLE 18

T & B Lymphocytes parameters improvement after ALF

|  | Patients No. | Improved No. | (%) |
|---|---|---|---|
| WBC | 25 | 18 | 72% |
| Lymphs | 34 | 25 | 74% |
| T11 | 32 | 21 | 66% |
| T4 | 30 | 24 | 80% |
| Ratio of T4/T8 | 46 | 37 | 80.4% |
| T8 | 52 | 40 | 76.9% |
| B4 | 35 | 27 | 77% |

TABLE 19

CMI Improvements of 93 Patients with ALF

| Total No. of Antigen Responses | |
|---|---|
| Increase | 247* |
| Decrease | 171 |
| No change | 233 |
| Total | 651 |

*$P < 0.001$ compared with decrease

TABLE 20

| Diagnosis | No. | % |
|---|---|---|
| Chemical sensitivity | 127 | 67 |
| Food Sensitivity | 106 | 56 |
| Inhalant Sensitivity | 84 | 44 |
| EMF Sensitivity | 9 | 5 |

TABLE 21

| Diagnosis | No. | % |
|---|---|---|
| N.S | 104 | 54.7 |
| C.V | 53 | 27.9 |
| G.I | 59 | 31.1 |
| G.U | 15 | 7.9 |
| M.S | 107 | 56.3 |
| EYE | 4 | 2.1 |
| Respiratory | 87 | 45.8 |
| Skin | 22 | 11.6 |
| Endocrine | 24 | 12.6 |
| Immune dysregulation | 99 | 52.1 |
| Chronic infectioin | 42 | 22.1 |
| Implant | 7 | 3.7 |
| Parasite | 3 | 1.6 |
| Carcinoma | 3 | 1.6 |
| Candidosis | 8 | 4.2 |
| HIV positive | 1 | 0.5 |

TABLE 22

50 Year Old White Female
HIV Positive
0.1 cc every 4 doses

|  | CMI before −1 | CMI after 3 |
|---|---|---|
| WBC | 3,500 | 10,000 |
| $T_{11}$ | 964 | 1359 |
| $T_{11\%}$ | 54 | 73% |
| $T_4$ | 149 | 750 |
| $T_{4\%}$ | 8% | 40% |
| T8 | 464 | 875 |
| $T_{8\%}$ | 26 | 47% |
| $T_4/T_8$ | .17 | 1.62 |
| B | 36 | 93 |
| B% | 2 | 5% |

| SX-fatigue, | Energy |
|---|---|
| neuropathy | gone |
| Stomach Pain | gone |
| Non healing toe | gone |
| Lesion for 2 yrs. | gone |

Took ALF for 5 months, then stopped
All Sx exacerbated for 3 weeks.
Restarted ALF and Sx disappeared

TABLE 23

PATIENTS WITH CANCER & ALF

| | 46 y F Breast Cancer Mar. 1, 1995 Sep. 3, 1996 0.1 cc 0.2 cc 90 doses | | 59 y F Breast Cancer Jun. 1, 1995 Jul. 21, 1995 0.1 cc 40 | | 84 y F Leukemia Oct. 20, 1994 Feb. 7, 1995 0.1 cc 60 | | 67 y F parathyroid tumor Mar. 25, 1996 Jan. 9, 1997 $1:10^3$-1:10 0.1 cc 130 | | 42 y F Breast Cancer Oct. 10, 1994 May 30, 1995 0.1 cc 90 | | 63 y F Left Breast Mastectomy Oct. 31, 1996 Jan. 10, 1997 0.1 cc 70 | | 23 y M Osteogenic Sarcoma Apr. 8, 1996 Sep. 24, 1996 0.1 cc 50 | |
|---|---|---|---|---|---|---|---|---|---|---|---|---|---|---|
| | B | A | B | A | B | A | B | A | B | A | B | A | B | A |
| Tetanus | 3 | | 0 | | | | 30 | | 5 | | 0 | | | |
| Diphtheria | 4 | | 0 | | | | 6 | | 4 | | 0 | | | |
| Streptococcus | 0 | | 0 | | | | 0 | | 0 | | 0 | | | |
| Tuberculin | 0 | | 0 | | | | 0 | | 0 | | 0 | | | |
| Control | 0 | | 0 | | | | 0 | | 0 | | 0 | | | |
| Candida | 0 | | 0 | | | | 0 | | 0 | | 0 | | | |
| Trichophyson | 0 | | 0 | | | | 0 | | 0 | | 0 | | | |
| Proteus | 0 | | 4 | | | | 0 | | 4 | | 0 | | | |
| WBC | 5100 | 6900 / 4300↓ / 4200↓ | | | 22300↑ | 7000 | | | 4700 | 5300 / 4500 | | 6700 | | |
| Lymphocytes | 2550 | 2277 / 1720 / 1848 | | | 15389↑ | 2590 | | | 1833 | 1431 / 1305 | | 2412 | | |
| Ly % | 50 | 33 / 40 / 44 | | | 69 | 37 | | | 39 | 27 / 29 | | 36 | | |
| $T_{11}$ | 1734 | 1867 / 1066↓ / 1478 | | | 4923↑ | 1868 | | | 1448 | 1188 / 861 | | 1787 | | |
| $T_{11}$ % | 68 | 82 / 62 / 80 | | | 32 | 76 | | | 79 | 83 / 66 | | 72 | | |
| $T_4$ | 944 | 1002 / 378↓ / 832 | | | 2308↑ | 1606 | | | 733 | 587 / 469 | | 724 | | |
| $T_4$ % | 37 | 44 / 22↓ / 45 | | | 15↓ | 62↑ | | | 40 | 41 / 36 | | 30 | | |
| $T_8$ | 612 | 433 / 482 / 591 | | | 2616↑ | 544 | | | 495 | 329 / 235 | | 699 | | |
| $T_8$ % | 24 | 19 / 28 / 32 | | | 17 | 21 | | | 27 | 23 / 18 | | 29 | | |
| $T_4/T_8$ | 15 | 2.32 / 0.79↓ / 1.41 | | | 0.9↓ | 2.95↑ | | | 1.5 | 1.8 / 2 | | 1.03 | | |
| $B_4$ | 332 | 205 / 120 / 92 | | | 1848↑ | 104 | | | 155 | 172 / 184 | | 241 | | |
| $B_4$ % | 13 | 9 / 7 / 5 | | | 12 | 4 | | | 9 | 12 / 8 | | 10 | | |

| | | A | A | | A | | | |
|---|---|---|---|---|---|---|---|---|
| Allergic | S | ↓ | | | 0 | | | |
| | F | ↓ | | | 0 | | | |
| Headaches | S | 0 | | | 0 | | | |
| | F | 0 | | | 0 | | | |
| Recurrent Infection | S | ↓ | | | 0 | | | |
| | F | ↓ | | | 0 | | | |
| Fatigue | S | ↓ | | | 0 | | | |
| | F | ↓ | | | 0 | | | |
| Difficulty Concentration | S | ↓ | | | 0 | | | |
| | F | 0 | | | 0 | | | |
| Arthritis | S | ↓ | | | 0 | | | |
| | F | ↓ | | | 0 | | | |

TABLE 23-continued

PATIENTS WITH CANCER & ALF

| GI Upset | S | ↓ | 0 |
|---|---|---|---|
| | F | ↓ | 0 |
| Depression | S | ↓ | 0 |
| | F | ↓ | 0 |

B: Before ALF
A: After ALF
S: Severity
F: Frequency

What is claimed is:

1. A method for treating a chemically sensitive individual having an irregular cell cycle for T lymphocytes, the method comprising the steps of:
   (a) collecting a blood sample from the individual;
   (b) determining an initial status of the cell cycle for T lymphocytes;
   (c) isolating mixed T and B lymphocytes from the blood sample;
   (d) propagating the isolated mixed T and B lymphocytes to obtain propagated lymphocytes;
   (e) lysing the propagated lymphocytes to obtain a lysate; and
   (f) administering the lysate to the individual.

2. The method according to claim 1, wherein the step of collecting a blood sample further comprises the step of: collecting the blood sample from the individual by venipuncture in heparinized tubes.

3. The method according to claim 1, wherein the step of isolating mixed T and B lymphocytes from the blood sample further comprises the steps of: separating the erythrocytes and neutrophils from the lymphocytes of the blood sample by a sodium diatrizoate and polysucrose density gradient technique to obtain a lymphocytic sample; centrifuging the lymphocytic sample; separating and combining the lymphocytic layers from the centrifuged lymphocytic sample; and washing the combined lymphocytic layers to obtain the isolated mixed T and B lymphocytes.

4. The method according to claim 1, wherein the step of propagating the isolated mixed T and B lymphocytes further comprises the steps of: culturing the isolated mixed T and B lymphocytes with a cell growth medium at about 37° C.

5. The method according to claim 4, wherein the cell growth medium is supplemented with bovine calf serum.

6. The method according to claim 4, wherein the step of propagating the lymphocytes further comprises the steps of: centrifuging the cultured lymphocytes; removing the supernate from the centrifuged lymphocytes; and washing the centrifuged lymphocytes in normal saline with further centrifugation to obtain the propagated lymphocytes.

7. The method according to claim 1, wherein the step of lysing the propagated lymphocytes further comprises the steps of: suspending the propagated lymphocytes in normal saline solution; sonicating the suspended lymphocytes; and filtering the sonicated lymphocytes to obtain the lysate.

8. The method according to claim 1, wherein the step of administering the lysate to the individual further comprises the step of: determining a therapeutic dose of the lysate by skin testing.

9. The method according to claim 8, wherein the step of administering the lysate to the individual comprises the step of: injecting the individual subcutaneously with the therapeutic dose of the lysate.

10. The method according to claim 9, further comprising the step of: injecting the individual subcutaneously with at least one additional therapeutic dose of the lysate.

11. The method according to claim 1, further comprising the steps of: measuring the clinical symptoms and signs of the individual before administering the lysate, and then measuring clinical symptoms and signs of the individual after administering the lysate.

12. A method for treating a chemically sensitive individual having an irregular cell cycle for T lymphocytes, the method comprising the steps of:
   (a) collecting a blood sample from the individual by venipuncture in heparinized tubes;
   (b) determining an initial status of the cell cycle for T lymphocytes;
   (c) isolating mixed T and B lymphocytes from the blood sample by:
      (i) separating the erythrocytes and neutrophils from the lymphocytes of the blood sample by a sodium diatrizoate and polysucrose density gradient technique to obtain a lymphocytic sample;
      (ii) centrifuging the lymphocytic sample;
      (iii) separating and combining the lymphocytic layers from the centrifuged lymphocytic sample; and
      (iv) washing the combined lymphocytic layers to obtain the isolated mixed T and B lymphocytes;
   (d) propagating the isolated mixed T and B lymphocytes to obtain propagated lymphocytes by:
      (i) culturing the isolated mixed T and B lymphocytes with a cell growth medium at about 37° C.;
      (ii) centrifuging the cultured lymphocytes;
      (ii) removing the supernate from the centrifuged lymphocytes; and
      (iv) washing the centrifuged lymphocytes in normal saline with further centrifugation to obtain the propagated lymphocytes;
   (e) lysing the propagated lymphocytes to obtain a lysate by:
      (i) suspending the propagated lymphocytes in normal saline solution;
      (ii) sonicating the suspended lymphocytes; and
      (iii) filtering the sonicated lymphocytes to obtain the lysate; and
   (f) administering the lysate to the individual by:
      (i) determining a therapeutic dose of the lysate by skin testing; and
      (ii) injecting the individual subcutaneously with the therapeutic dose of the lysate.

13. The method according to claim 12, wherein the cell growth medium is supplemented with bovine calf serum.

14. The method according to claim 12, wherein the culture is monitored until the yield is approximately $5-8 \times 10^6$ cells per ml.

15. The method according to claim 12, wherein the step of administering the lysate to the individual further comprises the step of: injecting the individual subcutaneously with at least one additional therapeutic dose of the lysate.

16. The method according to claim 12, further comprising the steps of: measuring the clinical symptoms and signs of the individual before administering the lysate, and then measuring clinical symptoms and signs of the individual after administering the lysate.

17. A method according to claim 1, wherein the step of determining the initial status of the cell cycle comprises the steps of: adding lysing buffer to a portion of the cell sample; adding DNA stain and RNAse to the portion of the cell sample; analyzing the portion of the DNA stained cell sample with flow cytometry to determine the DNA distribution in the cell cycle.

18. A method for treating a chemically sensitive individual, the method comprising the steps of:
   (a) collecting a blood sample from the individual;
   (b) determining an initial status of the cell cycle for T lymphocytes;
   (c) isolating mixed T and B lymphocytes from the blood sample;
   (d) propagating the isolated mixed T and B lymphocytes to obtain propagated lymphocytes;
   (e) lysing the propagated lymphocytes to obtain a lysate; and
   (f) administering the lysate to the individual.

* * * * *